(12) United States Patent
Zeman

(10) Patent No.: US 6,556,858 B1
(45) Date of Patent: Apr. 29, 2003

(54) DIFFUSE INFRARED LIGHT IMAGING SYSTEM

(76) Inventor: Herbert D. Zeman, 1687 Peach Ave., Memphis, TN (US) 38112

(*) Notice: Subject to any disclaimer, the term of this patent is extended or adjusted under 35 U.S.C. 154(b) by 0 days.

(21) Appl. No.: 09/487,007

(22) Filed: Jan. 19, 2000

(51) Int. Cl.[7] .................................................. A61B 6/00
(52) U.S. Cl. ....................... 600/473; 600/310; 600/476; 356/51; 250/330
(58) Field of Search ............................... 250/330, 338.1, 250/339.11, 339.14, 341.8; 348/77, 164; 356/51; 359/599; 600/407, 310, 473, 476

(56) References Cited

U.S. PATENT DOCUMENTS

| | | | |
|---|---|---|---|
| 4,817,622 A | | 4/1989 | Pennypacker et al. |
| 4,908,876 A | | 3/1990 | DeForest et al. |
| 4,947,850 A | * | 8/1990 | Vanderkooi et al. ........ 600/431 |
| 5,041,965 A | | 8/1991 | Chen |
| 5,231,434 A | | 7/1993 | Kennedy et al. |
| 5,353,075 A | | 10/1994 | Conner et al. |
| 5,359,550 A | | 10/1994 | Chen |
| 5,424,838 A | | 6/1995 | Siu |
| 5,519,208 A | | 5/1996 | Esparza et al. |
| 5,608,210 A | | 3/1997 | Esparza et al. |
| 5,757,544 A | * | 5/1998 | Tabata et al. ................ 359/385 |
| 5,772,593 A | * | 6/1998 | Hakamata ..................... 348/77 |
| 5,907,395 A | * | 5/1999 | Schulz et al. .......... 356/139.03 |
| 5,947,906 A | | 9/1999 | Dawson, Jr. et al. |
| 6,178,340 B1 | * | 1/2001 | Svetliza ....................... 250/226 |

FOREIGN PATENT DOCUMENTS

| | | |
|---|---|---|
| JP | 2172472 | 7/1990 |
| JP | 2172473 | 7/1990 |
| JP | 2174852 | 7/1990 |
| JP | 2174853 | 7/1990 |
| JP | 2174854 | 7/1990 |

OTHER PUBLICATIONS

Peli et al., Image Enhancement for the Visually Impaired, Investigative Ophthalmology & Visual Science, vol. 32, No. 8, Jul. 1991, pp. 2337–2350.
In Focus Systems, LitePro 620, http://www.infocus.com/products/projectors/lp620.html.
Texas Instruments, Digital Micromirror Device, http://www.ti.com/dlp/docs/papers/state/state.htm.

* cited by examiner

Primary Examiner—Marvin M. Lateef
Assistant Examiner—Runa Shoh Qaderi
(74) Attorney, Agent, or Firm—Luedeka, Neely & Graham, P.C.

(57) ABSTRACT

An imaging system illuminates body tissue with infrared light to enhance visibility of subcutaneous blood vessels, and generates a video image of the body tissue and the subcutaneous blood vessels based on reflected infrared light. The system includes an infrared light source for generating the infrared light and a structure for diffusing the infrared light. The diffusing structure has an input aperture for receiving the infrared light from the infrared light source, and multiple interior reflecting surfaces. The reflecting surfaces reflect the infrared light multiple times and in multiple directions, thereby producing diffuse infrared light. The diffusing structure also has an output aperture for receiving the diffuse infrared light reflected from the plurality of reflecting surfaces and for emitting the diffuse infrared light toward the body tissue. The system further includes a video imaging device for receiving the infrared light reflected from the body tissue and for generating a video image of the body tissue based on the reflected infrared light.

16 Claims, 9 Drawing Sheets

DIFFUSE INFRARED LIGHT IMAGING SYSTEM

TECHNICAL FIELD

The present invention is generally directed to generation of diffuse infrared light. More particularly, the invention is directed to a system for illuminating an object with diffuse infrared light and producing a video image of the object based on reflected infrared light.

BACKGROUND OF THE INVENTION

Some medical procedures and treatments require a medical practitioner to locate a blood vessel in a patient's arm or other appendage. This can be a difficult task, especially when the blood vessel lies under a significant deposit of subcutaneous fat. The performance of previous imaging systems designed to aid in finding such blood vessels has been lacking.

Therefore, a system for enhancing the visual contrast between subcutaneous blood vessels and surrounding tissue is needed.

SUMMARY OF THE INVENTION

The foregoing and other needs are met by an imaging system for viewing body tissue under diffuse infrared illumination to enhance visibility of subcutaneous blood vessels. The imaging system includes an illumination system for illuminating the body tissue with infrared light that arrives at the body tissue from a plurality of different illumination directions. Thus, the illumination system provides diffuse infrared light to the body tissue. The imaging system also includes a video imaging device for viewing the body tissue, for receiving the diffuse infrared light reflected from the body tissue, and for generating a video image of the body tissue based on the diffuse infrared light reflected from the body tissue.

Using the invention described herein, subcutaneous blood vessels that are difficult or impossible to see under white light or under non-diffuse infrared light can be easily seen in the video image, where the subcutaneous blood vessels appear as dark lines against a lighter background of surrounding flesh.

In preferred embodiments of the invention, the illumination system includes an infrared light source for generating the infrared light and a light diffusing structure for diffusing the infrared light. The diffusing structure has an input aperture for receiving the infrared light from the infrared light source, and multiple interior reflecting surfaces. The reflecting surfaces reflect the infrared light multiple times and in multiple directions, thereby producing diffuse infrared light. The diffusing structure also has an output aperture for receiving the diffuse infrared light reflected from the plurality of reflecting surfaces and for emitting the diffuse infrared light toward the body tissue. The system further includes a video imaging device for receiving the diffuse infrared light reflected from the body tissue and for generating a video image of the body tissue based on the reflected infrared light.

In some preferred embodiments, the diffusing structure includes an elongate outer enclosure having reflective inner surfaces, and an elongate inner enclosure disposed within the outer enclosure. The inner enclosure has reflective outer surfaces facing the inner surfaces of the outer enclosure.

In other preferred embodiments, the invention provides an illumination system for enhancing visual contrast between bright and dark areas of an object as sensed by a direct observer of the object. The system includes an infrared light source for generating infrared light, and a structure for diffusing the infrared light. The diffusing structure has an input aperture for receiving the infrared light from the infrared light source, and multiple reflecting surfaces for reflecting the infrared light multiple times and in multiple directions, thereby producing diffuse infrared light. The diffusing structure also has an output aperture for receiving the diffuse infrared light reflected from the reflecting surfaces and for emitting the diffuse infrared light toward the object. The system further includes a video imaging device for measuring diffuse infrared light reflected from the object in the form of an image, and for creating a video output signal representative of the image. A video projector receives the video output signal from the video imaging device and projects visible video projector light onto the object, thereby forming a visual image which is representative of the visual image received by the video imaging device. The visual image projected by the video projector illuminates the object from the same perspective that the video imaging device views the object. Thus, features of the projected visual image overlay the corresponding features of the object. The system includes a filter for distinguishing between the diffuse infrared light and the visible video projector light. The filter prevents the visible video projector light from reaching the video imaging device while allowing the diffuse infrared light reflected from the object to reach the video imaging device. Thus, the filter eliminates positive feedback which would degrade the desired visual effect.

In yet another aspect, the invention provides a method for viewing body tissue under infrared illumination to enhance visibility of subcutaneous blood vessels. The method includes the step of providing infrared light to the body tissue from multiple different illumination directions, thereby illuminating the body tissue with diffuse infrared light. The method also includes viewing the body tissue from a viewing direction using a video imaging device, and generating a video image of the body tissue based on diffuse infrared light reflected from the body tissue. Using the video image of the body tissue, the subcutaneous blood vessels may be found.

BRIEF DESCRIPTION OF THE DRAWINGS

Further advantages of the invention will become apparent by reference to the detailed description of preferred embodiments when considered in conjunction with the drawings, which are not to scale, wherein like reference characters designate like or similar elements throughout the several drawings as follows:

FIG. 6b is a cross-sectional view of the imaging system of FIG. 6a;

FIG. 7b is a cross-sectional view of the imaging system of FIG. 7a.

DETAILED DESCRIPTION OF THE PREFERRED EMBODIMENT

Skin and some other body tissues reflect infrared light in the near-infrared range of about 700 to 900 nanometers, while blood absorbs radiation in this range. Thus, in video images of body tissue taken under infrared illumination, blood vessels appear as dark lines against a lighter background of surrounding flesh. However, due to the reflective nature of subcutaneous fat, blood vessels that are disposed below significant deposits of such fat can be difficult or impossible to see when illuminated by direct light, that is, light that arrives generally from a single direction.

The inventor has determined that when an area of body tissue having a significant deposit of subcutaneous fat is imaged in near-infrared range under illumination of highly diffuse infrared light, there is significantly higher contrast between the blood vessels and surrounding flesh than when the tissue is viewed under direct infrared illumination. Although the invention should not be limited by any particular theory of operation, it appears that most of the diffuse infrared light reflected by the subcutaneous fat is directed away from the viewing direction. Thus, when highly diffuse infrared light is used to illuminate the tissue, the desired visual contrast between the blood vessels and the surrounding flesh is maintained.

Figure 1:
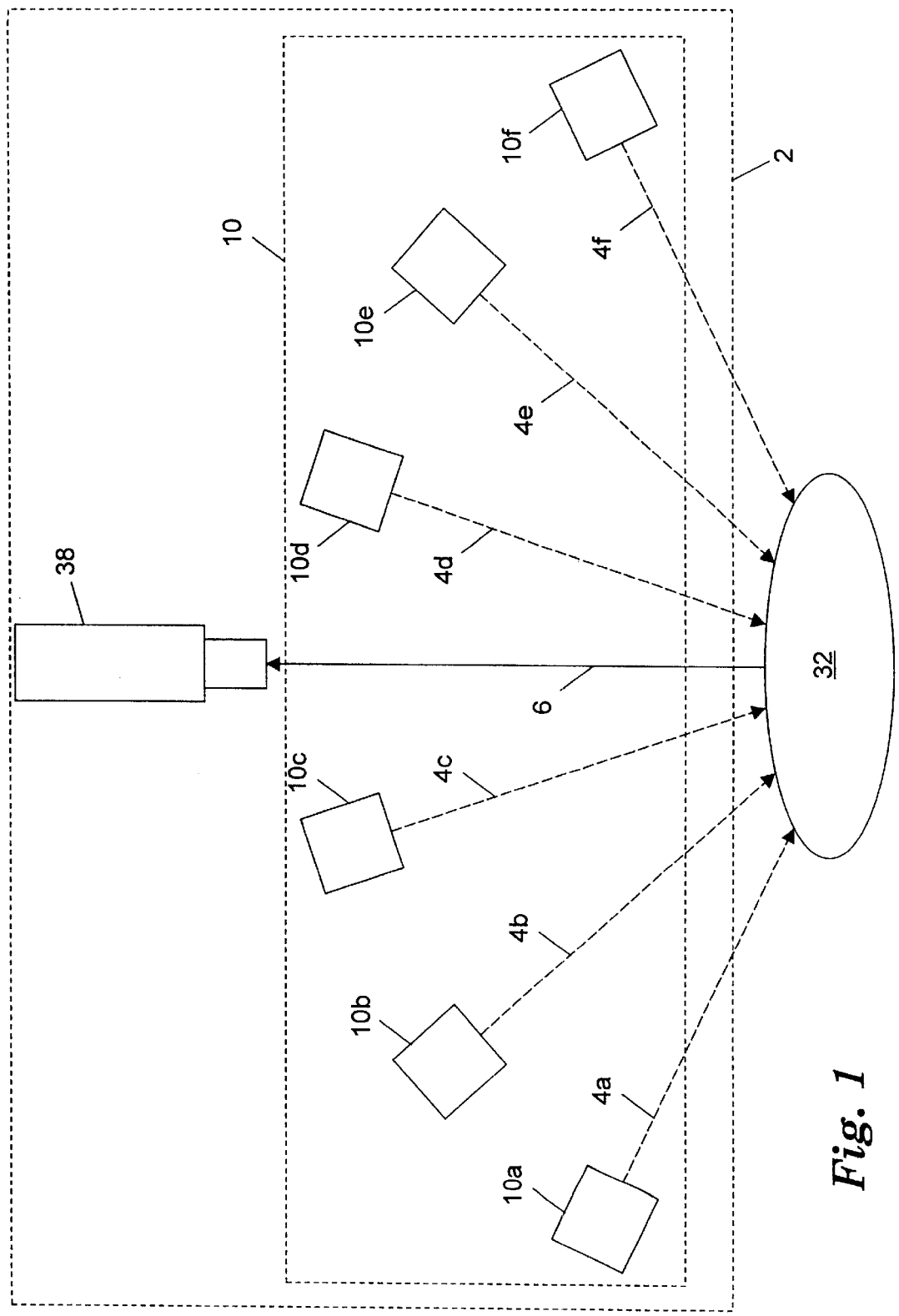
FIG. 1 depicts an imaging system for viewing an object under infrared illumination according to a preferred embodiment of the invention.

Shown in FIG. 1 is an imaging system 2 for illuminating an object 32, such as body tissue, with highly diffuse infrared light, and for producing a video image of the object 32 based upon infrared light reflected from the object 32. As described in detail herein, when the object 32 is body tissue, blood vessels that are disposed below subcutaneous fat in the tissue may be clearly seen in a video image produced by the system 2.

The imaging system 2 includes an illumination system 10 that illuminates the object 32 with infrared light from multiple different illumination directions. The system 10 includes multiple infrared light providers 10a–10f, each providing infrared light to the object 32 from a different illumination direction. The directions of arrival of the infrared light from each light provider 10a–10f are represented in FIG. 1 by the rays 4a–4f. As shown in FIG. 1, the directions of arrival of the infrared light ranges from perpendicular or near perpendicular to the surface of the object 32, to parallel or near parallel to the surface of the object 32. Since the infrared illumination arrives at the object 32 from such a wide range of illumination directions, the infrared illumination is highly diffuse.

As described in greater detail hereinafter, the light providers 10a–10f are preferably light reflecting surfaces that direct light from a single light source toward the object 32. In other embodiments, the light providers 10a–10f are individual light sources, or combinations of light sources and reflectors.

The imaging system 2 also includes an imaging device 38, such as a video camera, for viewing the object 32. The imaging device 38 views the object 32 from a viewing direction which is represented in FIG. 1 by the arrow 6. The imaging device 38 receives the diffuse infrared light reflected from the object 32, and generates an electronic video image of the object 32 based on the reflected infrared light.

Figure 2:
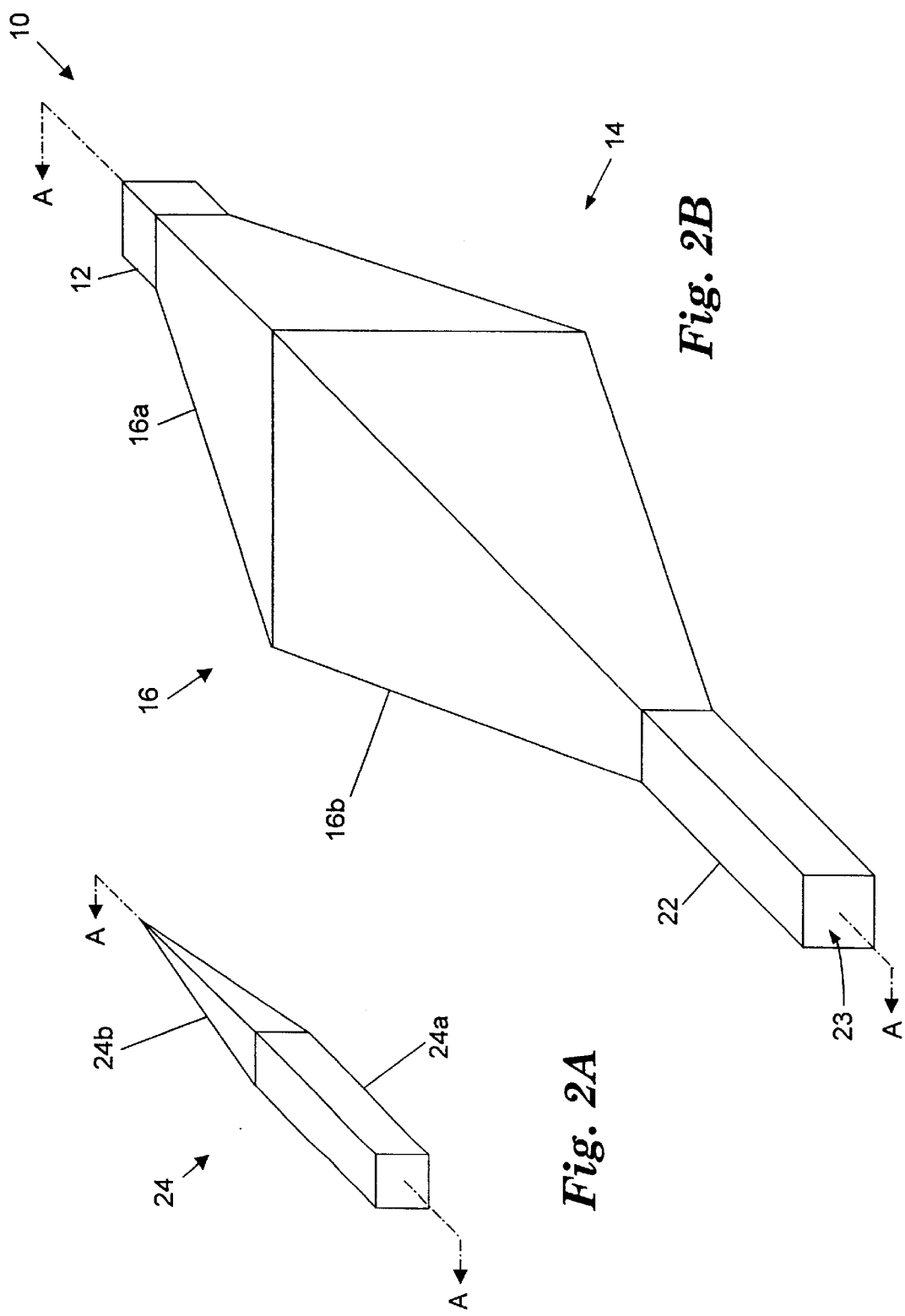
FIGS. 2a and 2b are perspective views of an imaging system using diffuse infrared light according to a preferred embodiment of the invention.
Figure 3:
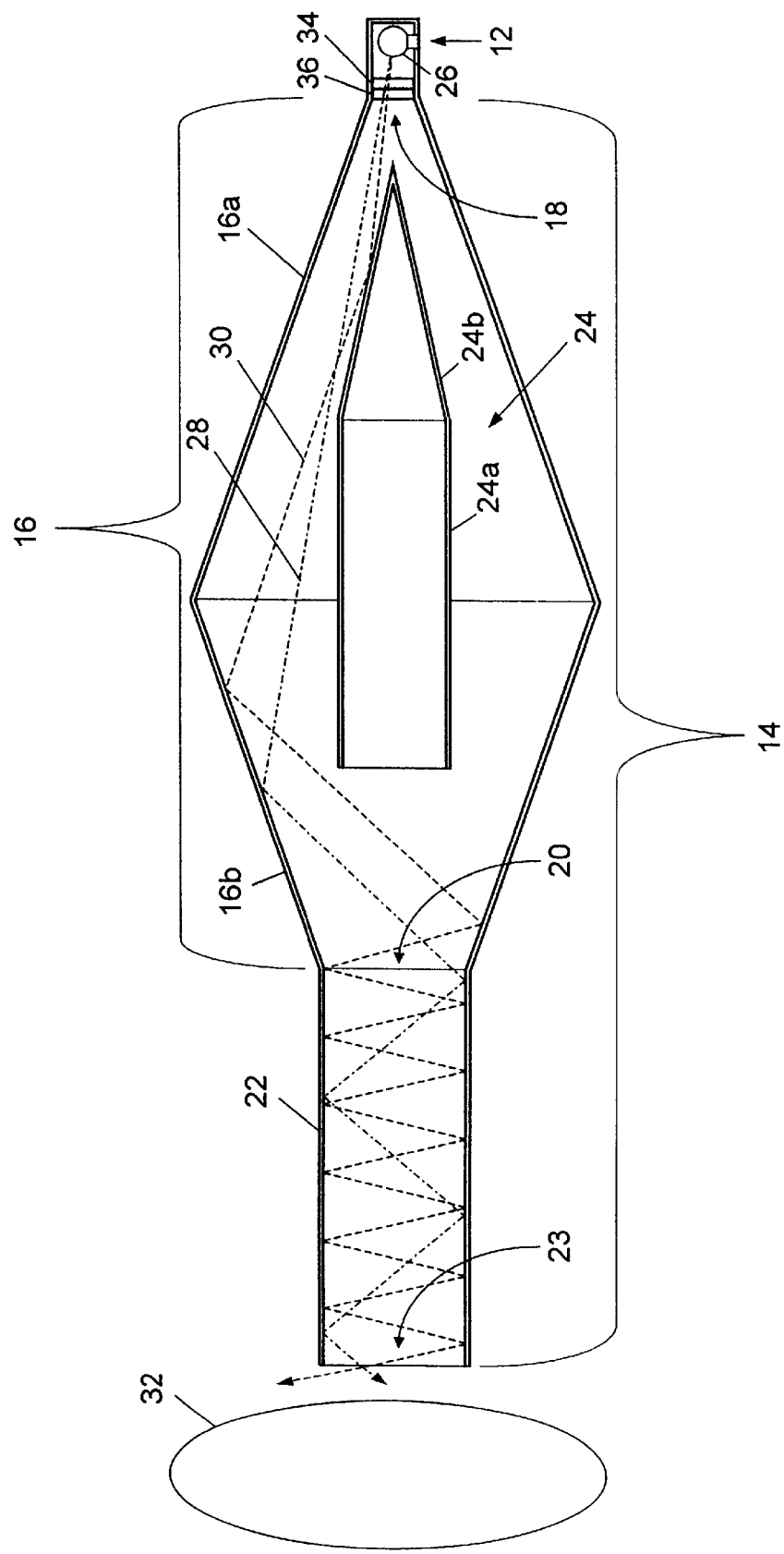
FIGS. 3 and 4 are cross-sectional views of the imaging system according to a preferred embodiment of the invention.

Shown in FIGS. 2a and 2b is a preferred embodiment of the illumination system 10. FIG. 3 depicts a cross-sectional view of the system 10 corresponding to the section A—A as shown in FIGS. 2a–b. The system 10 preferably includes a light source 12 that emits light into one end of a light diffusing structure 14. The light diffusing structure 14 includes an elongate outer enclosure 16 having reflective inner surfaces. Preferably, the inner surfaces of the elongate outer enclosure 16 are white in color. Alternatively, these reflective surfaces are mirrored surfaces, or a combination of white and mirrored surfaces. At the end of the light diffusing structure 14 opposite the light source 12, is a hollow light guide 22. As described in more detail below, the light guide 22 serves as an output aperture for the diffuse light.

The elongate outer enclosure 16 includes first and second sections 16a and 16b, each having a large end and a small end. Preferably, the first and second sections 16a and 16b are substantially pyramidal in shape, each having four trapezoidal faces. In the preferred embodiment, the four trapezoidal faces of the sections 16a and 16b are identical, such that each end of the sections 16a and 16b forms a square aperture. As shown in FIG. 2b, the larger ends of the first and second sections 16a and 16b are joined together to form the enclosure 16.

At the small end of the first section 16a is an input aperture 18 formed by the four short sides of the four trapezoidal faces of the section 16a. The light source 12 is preferably attached to the small end of the first section 16a at the input aperture 18. Thus, the light generated by the light source 12 enters the elongate enclosure 16 at the input aperture 18, and illuminates the interior surfaces of the enclosure 16.

At the small end of the second section 16b is an output aperture 20 formed by the four short sides of the four trapezoidal faces of the section 16b. Attached at the output aperture 20 is one end of the hollow light guide 22. The light guide 22 preferably has white reflective inner surfaces similar to the inner surfaces of the enclosure 16.

The system 10 also includes an elongate inner reflector 24 which is disposed within and preferably coaxial with the outer enclosure 16. For clarity, the inner reflector 24 is shown in FIG. 2a removed from the outer enclosure 16. In the preferred embodiment, the inner reflector 24 is formed from a square tubular section 24a joined to the square base of a pyramidal section 24b. Preferably, the pyramidal section 24b has four sides that taper down to an apex. As shown in FIG. 3, the apex of the pyramidal section 24b is disposed proximate the input aperture 18 of the outer enclosure 16. The inner reflector 24 has reflective white outer surfaces similar to those of the inner surfaces of the outer enclosure 16.

The light diffusing characteristics of the structure 14 are best understood with reference to FIG. 3. Within the light source 12 is a lamp 26, such as a quartz-halogen bulb and gold-plated reflector manufactured by Gilway and having part number L517A-G. When energized, the lamp 26 produces electromagnetic radiation in the form of white light.

For purposes of this description, the lamp 26 may be thought of as a point source radiating light in multiple directions, as represented by the exemplary rays 28 and 30. As shown in FIG. 3, the ray 28 reflects from the inner surface of the section 16b of the outer enclosure 16. The ray 28 then travels through the output aperture 20, into the light guide 22, and, after multiple reflections from the inner surfaces of the light guide 22, emits from the exit aperture 23. The ray 30, which exits the light source 12 from a different angle than the ray 28, reflects from the inner reflector 24. The ray 30 then reflects from the inner surface of the section 16b of the outer enclosure 16, and travels through the output aperture 20 and into the light guide 22. After multiple reflections from the inner surfaces of the light guide 22, the ray 30 also emits from the exit aperture 23, but at a different angle than that of the ray 28.

When an object 32 is placed near the exit aperture 23, the rays 28 and 30 arrive at the object 32 from different angles. It will be appreciated that the light radiating from the light source 12 could be represented as an infinite number of rays which strike and reflect from the inner reflector 24 and the inner surfaces of the outer enclosure 16 from an infinite number of angles. Thus, the light emitted from the exit aperture 23 arrives at the object 32 from many different angles, and is therefore highly diffuse light. These arrival angles range from near perpendicular to near parallel with the plane of the exit aperture 23. Since the diffusing structure 14 is three-dimensional, it will be appreciated that light also reflects from the other surfaces of the outer enclosure 16 and the inner reflector 24, such as those that are perpendicular to the surfaces shown in FIG. 3. Therefore, the light emitted at the exit aperture 23 of the illumination system 10 is highly diffuse, appearing to be generated by many different light sources.

Due to the arrangement of the reflective inner surfaces of the outer enclosure 16 and the reflective outer surfaces of the inner reflector 24, the diffusing structure 14 efficiently transfers the light radiated from the lamp 26 to the exit aperture 23. Thus, a very large fraction of the light provided by the lamp 26 reaches the object 32, and very little light energy is wasted.

As described in more detail below, the illumination system 10 can be used to provide diffuse light for medical imaging purposes. However, it will be appreciated that the scope of the invention is not limited to medical uses. The system 10 could also be used as a diffuse light source for general photographic purposes.

In a preferred embodiment of the invention, as depicted in FIG. 3, the light source 12 includes a cold mirror 34 disposed between the lamp 26 and the input aperture 18 of the outer enclosure 16. The cold mirror 34 reflects substantially all light having wavelengths outside a selected infrared range of wavelengths. Preferably, the selected range includes wavelengths from approximately 700 to 1000 nanometers. Immediately proximate the cold mirror 34, and disposed between the cold mirror 34 and the input aperture 18, is an infrared transmitting filter 36 which further attenuates light having wavelengths outside the selected infrared range while transmitting light having wavelengths within the selected infrared range. Thus, the light that passes through the cold mirror 34 and the filter 36 into the outer enclosure 16 is infrared light having wavelengths within the selected infrared range.

It should be appreciated that there are other ways that the light source 12 could be configured to generate infrared light. For example, the light source 12 could consist of an infrared light-emitting diode (LED) or an array of infrared LED's. Thus, the configuration of the light source 12 shown in FIG. 3 and described above is a preferred embodiment only, and the invention is not limited to any particular configuration of the light source 12.

Figure 4:
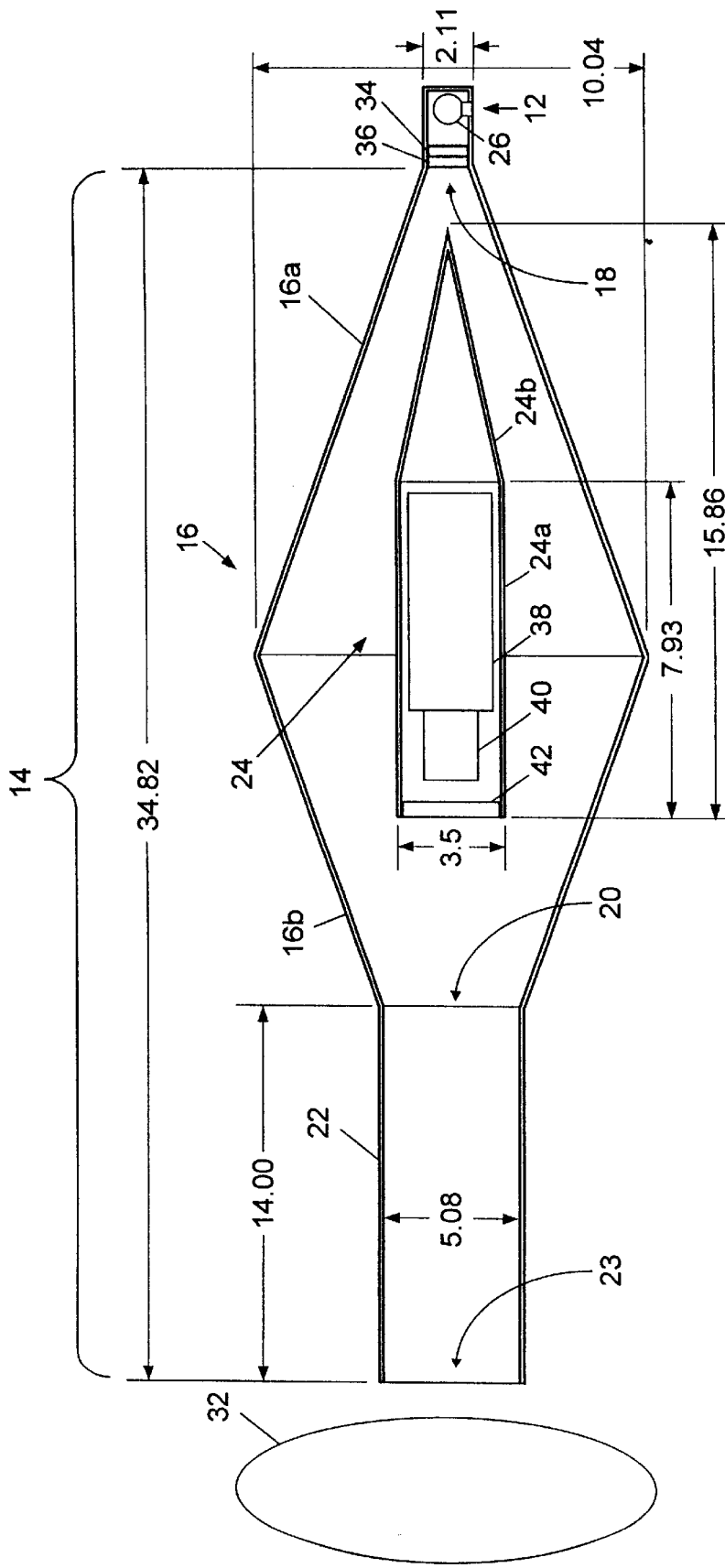

FIG. 4 depicts the dimensions of a preferred embodiment of the illumination system 10. As shown in FIG. 4, the total length of the light diffusing structure 14 is approximately 34.82 inches. The height and width of the outer enclosure 16 at the juncture of the first and section sections 16a and 16b is approximately 10.04 inches. The preferred length of the light guide 22 is approximately 14.00 inches, and its height and width is approximately 5.08 inches. Preferably, the total length of the inner reflector 24 is approximately 15.86 inches. The preferred length of the tubular section 24a of the inner reflector 24 is approximately 7.93 inches. The height and width of the tubular section 24a is approximately 3.5 inches. The height and width of the light source 12 is approximately 2.11 inches.

As shown in FIG. 4, a preferred embodiment of the invention includes a lens 40 used in conjunction with the video imaging device 38 to produce a video image of the object 32 based on diffuse light reflected from the object 32. Preferably, the imaging device 38 of this embodiment is a charge-coupled device (CCD) video camera 38 manufactured by Cohu, having model number 631520010000. The lens 40 of the preferred embodiment is a 25 mm f-0.95 movie camera lens manufactured by Angenieux.

The camera 38 and lens 40 of the preferred embodiment are disposed within the tubular section 24a of the inner reflector 24. As shown in FIG. 4, the open end of the tubular section 24a forms an aperture toward which the camera 38 and lens 40 are pointed. In this manner, the hollow light guide 22 is substantially centered within the field of view of the camera 38. Thus, the camera 38 receives light reflected from the object 32 that enters the light guide 22, travels through the enclosure 16, and enters the open end of the section 24a.

As shown in FIG. 4, the preferred embodiment of the invention includes an infrared-transmitting filter 42 disposed in the open end of the tubular section 24a. This filter 42 receives light reflected from the object 32, and any other light that may enter the enclosure 16, and substantially eliminates all light having wavelengths outside the infrared range of approximately 700 to 1000 nanometers. In the preferred embodiment, the filter 42 substantially eliminates light having wavelengths outside a selected infrared range of approximately 800 to 850 nanometers. Thus, the light that passes through the filter 42 and into the lens 40 is infrared light within the selected wavelength range. Therefore, the camera 38 primarily receives infrared light which originates from within the illumination system 10 and which is reflected from the object 32.

Figure 5:
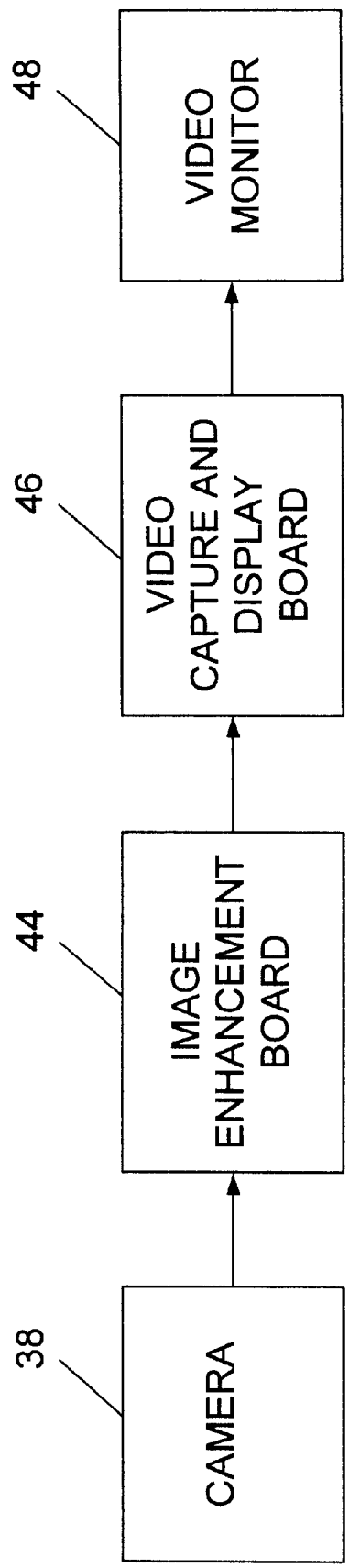
FIG. 5 is a functional block diagram of the imaging system according to a preferred embodiment of the invention.

Based on the light reflected from the object 32, the camera 38 generates a video image of the object 32 in the form of an electrical video signal. As shown in FIG. 5, the video signal is preferably provided to an image enhancement board 44, such as a board manufactured by DigiVision having a model number ICE-3000. The board 44 generates an enhanced video image signal based on the video signal from the camera 38. The enhanced video image signal is provided to a video capture and display card 46, such as a model 20TDLive card manufactured by Miro. The card 46 captures still images from the image signal which may be saved in digital format on a digital storage device. The card 46 also formats the video image signal for real-time display on a video monitor 48.

It should be appreciated that the illumination system 10 could use other means for generating diffuse infrared light in accordance with the invention. For example, the light providers 10a–10f of FIG. 1 could be embodied by a ring-light strobe light. Alternatively, a circular array of LED's could be used to illuminate a plastic transmitting diffuser placed near the surface of the object 32. In the latter embodiment, the light providers 10a–10f would correspond to the individual LED's in the array.

Figure 6A:
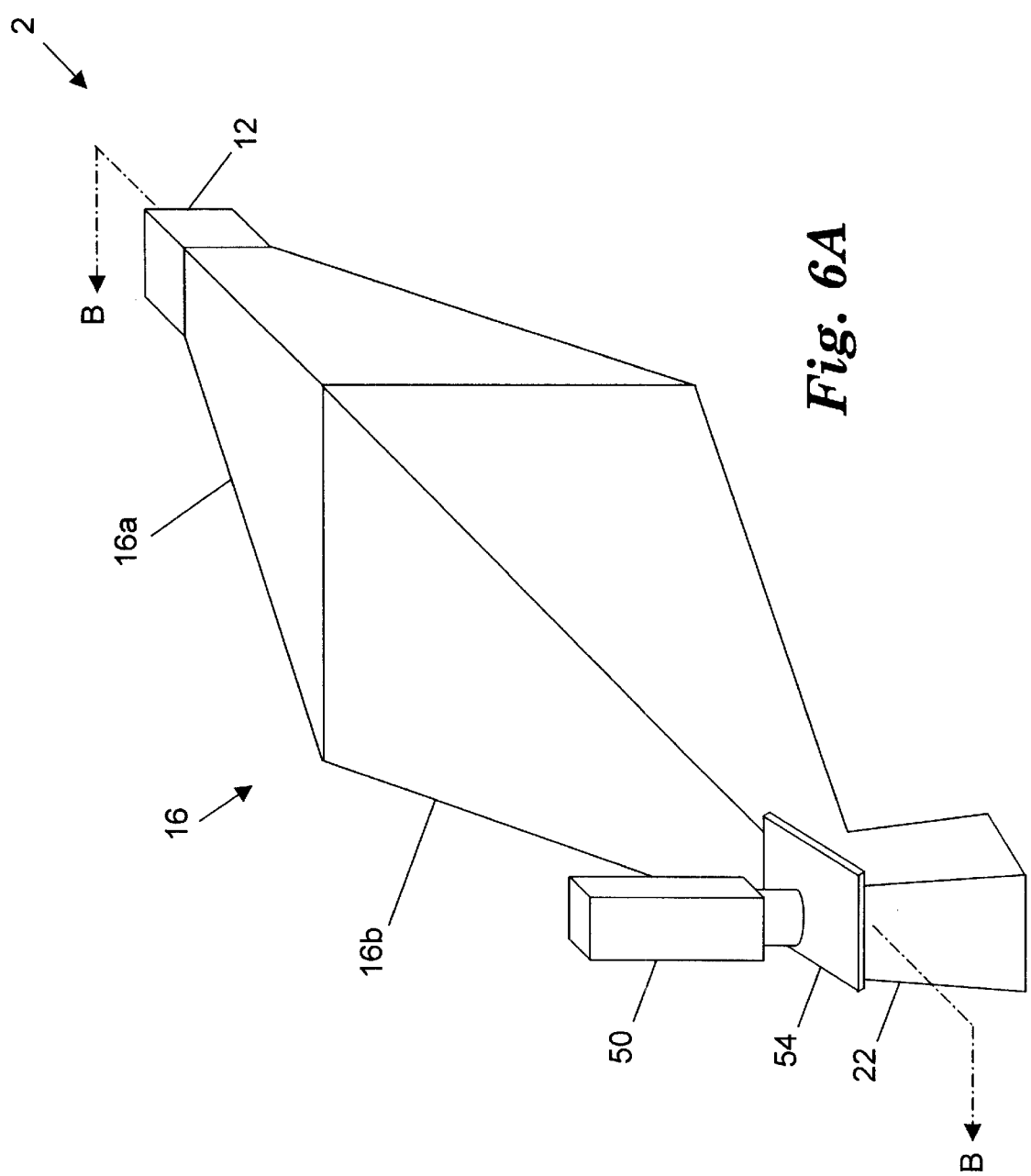
FIG. 6a is a perspective view of an imaging system using diffuse infrared light according to an alternative embodiment of the invention.
Figure 6B:
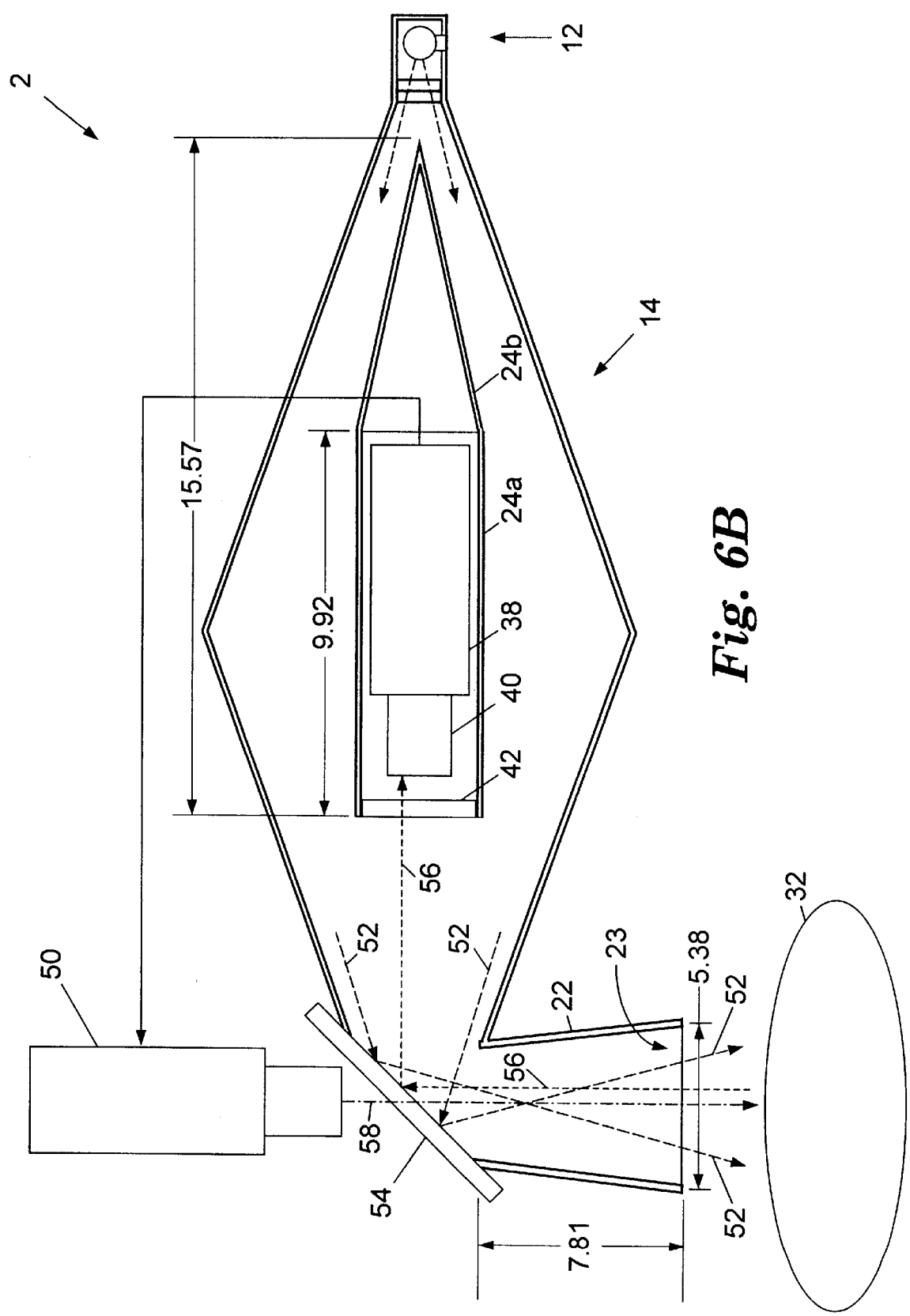

In an alternative embodiment of the invention depicted in FIGS. 6a and 6b, the imaging system 2 includes a video projector 50 for illuminating the object 32 with an image of the object 32 to enhance the visual contrast between lighter and darker areas of the object 32. As described in U.S. Pat. No. 5,969,754, entitled CONTRAST ENHANCING ILLUMINATOR, the contents of which are incorporated herein by reference, the features of an object are visually enhanced for an observer when the features of a projected visible-light image of the object overlay the corresponding features of the object. The overlaid visible-light image causes the bright features of the object to appear brighter while the dark areas remain the same.

The embodiment of the invention shown in FIGS. 6a and 6b provides diffuse infrared light (represented by the rays 52) to the object 32 in a manner similar to that described previously. However, in the embodiment shown in FIGS. 6a and 6b, the optical path of the illuminating light is folded, such that the exit aperture 23 of the light guide 22 is rotated by 90 degrees relative to the exit aperture shown in FIGS. 1–3.

As shown in FIG. 6b, a beam separator, such as a hot mirror 54, receives infrared light 52 from the interior of the light diffusing structure 14 and reflects the infrared light 52 into the light guide 22 and toward the object 32. The hot mirror 54 also receives an infrared image of the object 32 (represented by the ray 56) and reflects it toward the camera 38. The hot mirror 54 receives the visible-light image (represented by the ray 58) from the projector 50 and transmits it into the light guide 22 and toward the object 32.

As explained in greater detail in U.S. Pat. No. 5,969,754, the video output signal from the video camera 38 is provided as a video input signal to the projector 50. Based on the video input signal, the projector 50 projects the visible-light image 58 of the object 32 toward the hot mirror 54. The hot mirror 54 receives the visible-light image 58 and transmits it into the light guide 22 toward the object 32. By proper alignment of the projected visible-light image 58 from the projector 50 with the infrared image 56 of the object 32 which is sensed by the camera 38, the features in the projected visible-light image 58 are made to overlay the corresponding features of the object 32.

When the object 32 is body tissue, and the invention is used to find subcutaneous blood vessels in the body tissue, the blood vessels appear as dark lines in the projected visible-light image 58. Thus, when the visible-light image 58 is projected onto the body tissue, the subcutaneous blood vessels will lie directly beneath the dark lines in the projected visible-light image 58. In this manner, the invention significantly improves a medical practitioner's ability to find subcutaneous blood vessels while minimizing discomfort for the patient.

Figure 7A:
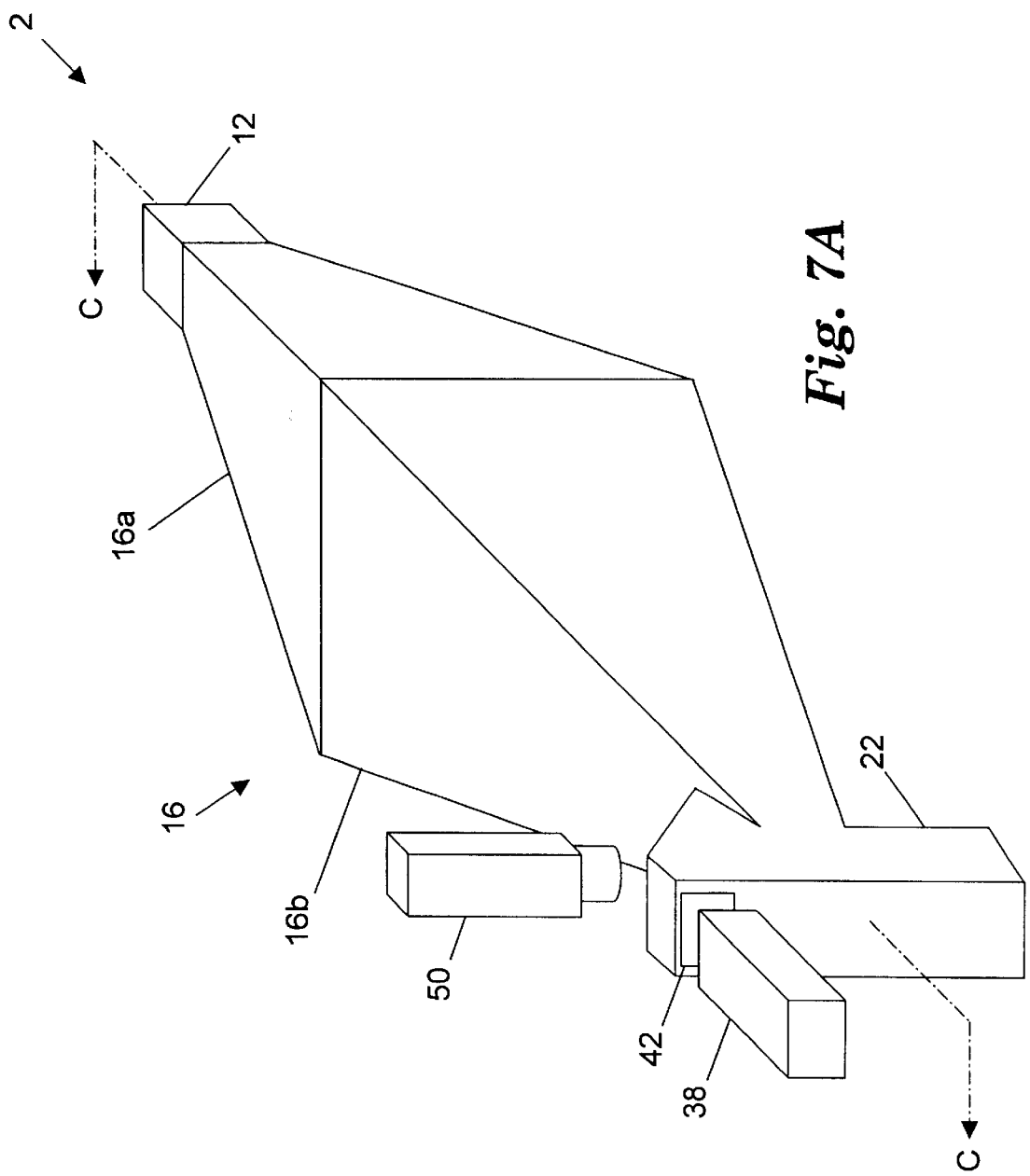
FIG. 7a is a perspective view of an imaging system using diffuse infrared light according to another embodiment of the invention.
Figure 7B:
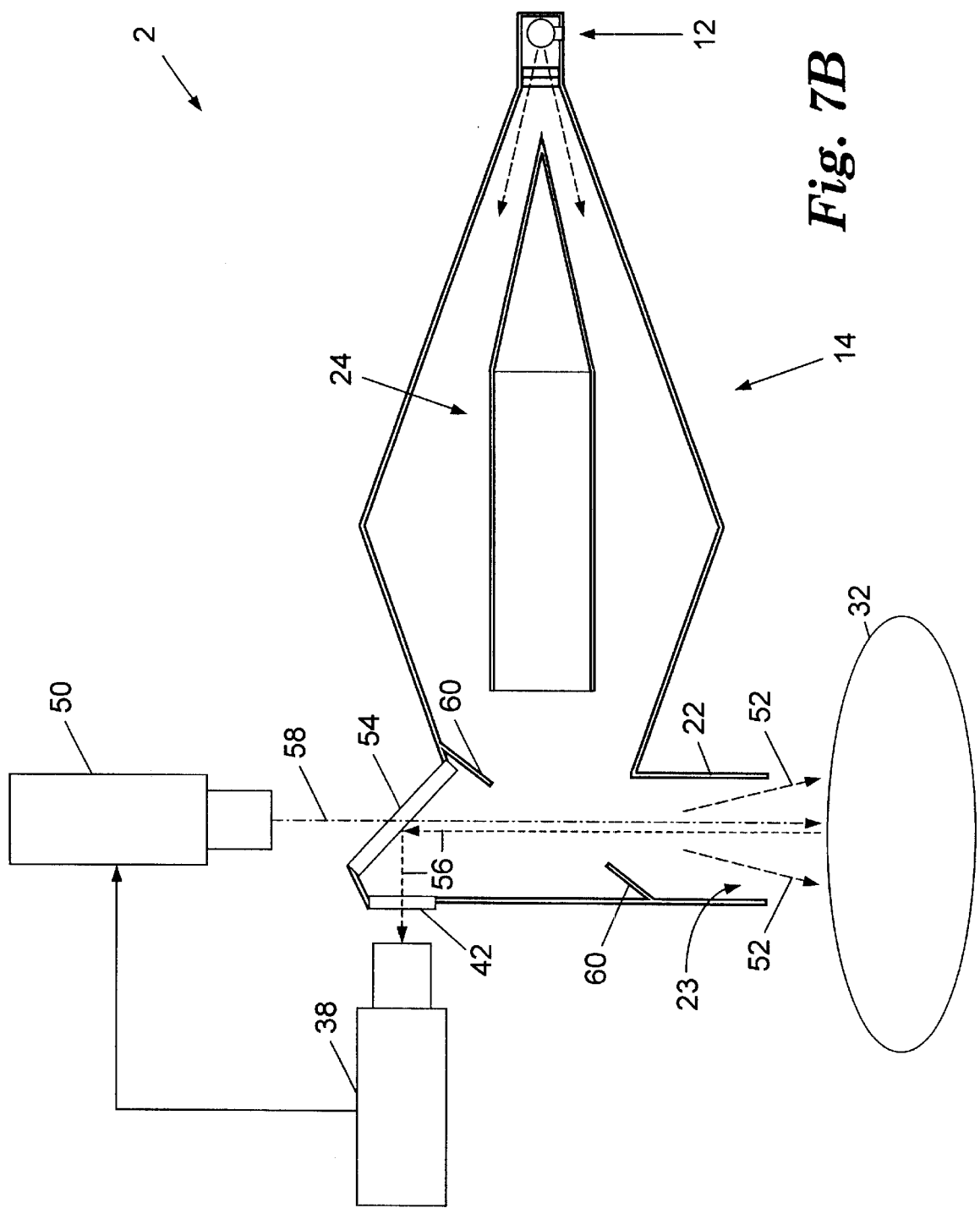

FIGS. 7a and 7b depict an alternative embodiment of the invention for use as a contrast enhancing illuminator. The embodiment of FIGS. 7a–b operates in a fashion similar to the embodiment of FIGS. 6a and 6b. However, in the embodiment of FIGS. 7a–b, the camera 38 is located outside the light diffusing structure 14. To accommodate the different location of the camera 38, the hot mirror 54 shown in FIGS. 7a–b is rotated by 90 degrees clockwise relative to its position in FIGS. 6a–b. Otherwise, the hot mirror 54 serves a similar function as that described above in reference to FIGS. 6a–b. Also to accommodate the different camera location, the infrared-transmitting filter 42 is mounted in a wall of the light guide 22. A reflective panel 60 is provided in this embodiment to further direct the light from the light source 12 into the light guide 22 and toward the exit aperture 23. Preferably, the panel 60 is a flat reflective sheet having an orifice therein to allow light to pass between the object 32 and the camera 38 and projector 50.

It is contemplated, and will be apparent to those skilled in the art from the preceding description and the accompanying drawings that modifications and/or changes may be made in the embodiments of the invention. For example, the sections 16a and 16b of the outer enclosure could be conical rather than pyramidal. Further, the section 24a of the inner reflector could be cylindrical and the section 24b could be conical. Alternatively, the sections 16a–b and 24b could be pyramidal and have more than four trapezoidal faces. Thus, it should be appreciated that the invention is not limited to any particular shape of the reflectors 24 and 16. Accordingly, it is expressly intended that the foregoing description and the accompanying drawings are illustrative of preferred embodiments only, not limiting thereto, and that the true spirit and scope of the present invention be determined by reference to the appended claims.

What is claimed is:

1. An imaging system for viewing body tissue under infrared illumination to enhance visibility of subcutaneous blood vessels, the system comprising:

means for illuminating the body tissue with infrared light from a plurality of different illumination directions, thereby providing diffuse infrared light to the body tissue, comprising:
an infrared light source for generating the infrared light; and
means for diffusing the infrared light having:
an elongate outer enclosure having reflective inner surfaces, and having a first outer enclosure end and a second outer enclosure end;
an input aperture disposed at the first outer enclosure end for receiving the infrared light from the infrared light source;
a plurality of reflecting surfaces for reflecting the infrared light multiple times and in multiple reflection directions, thereby producing diffuse infrared light; and
an output aperture disposed at the second outer enclosure end for receiving the diffuse infrared light reflected from the plurality of reflecting surfaces and for emitting the diffuse infrared light toward the body tissue; and
an elongate inner enclosure disposed within the outer enclosure and between the first and second outer enclosure ends, the inner enclosure having reflective outer surfaces facing the inner surfaces of the outer enclosure; and
video imaging means for viewing the body tissue from a viewing direction, for receiving the diffuse infrared light reflected from the body tissue, and for generating a video image of the body tissue based on the diffuse infrared light reflected from the body tissue.

2. The system of claim 1 further comprising:
the elongate inner enclosure having:
a first inner enclosure end disposed proximate the first outer enclosure end;
a second inner enclosure end disposed proximate the second outer enclosure end; and
an inner enclosure aperture disposed at the second inner enclosure end; and
the video imaging means disposed within the inner enclosure for receiving the diffuse infrared light reflected from the body tissue through the inner enclosure aperture.

3. The system of claim 2 further comprising:
  filter means disposed at the inner enclosure aperture for receiving light reflected from the body tissue, and for attenuating any portion of the light having wavelengths outside an infrared range of wavelengths to produce filtered infrared light; and
  the video imaging means for receiving the filtered infrared light from the filter means, and for generating the video image of the object based on the filtered infrared light.

4. The system of claim 1 wherein the elongate outer enclosure further comprises:
  a first substantially pyramidal section having a small first pyramidal section end and a large first pyramidal section end, the first outer enclosure end incorporating the small first pyramidal section end;
  a second substantially pyramidal section having a large second pyramidal section end and a small second pyramidal section end, the large second pyramidal section end adjoined to the large first pyramidal section end; and
  an outer tubular section having a first outer tubular section end and a second outer tubular section end, the first outer tubular section end adjoined to the large second pyramidal section end, the second outer enclosure end incorporating the second outer tubular end.

5. The system of claim 4 wherein the elongate inner enclosure further comprises:
  a third pyramidal section having a small third pyramidal section end and a large third pyramidal section end, the first inner enclosure end incorporating the small third pyramidal section end; and
  an inner tubular section having a first inner tubular section end and a second inner tubular section end, the first inner tubular section end adjoined to the large third pyramidal section end, and the second inner enclosure end incorporating the second inner tubular section end.

6. The system of claim 1 further comprising:
  a video projector for projecting a visible light image of the body tissue based on the video image of the body tissue generated by the video imaging means; and
  a beam separator for receiving the diffuse infrared light from the output aperture and reflecting the diffuse infrared light toward the body tissue, for receiving the visible light image from the video projector and transmitting the visible light image toward the body tissue, and for receiving the infrared light reflected from the body tissue and reflecting the light reflected from the body tissue toward the video imaging means.

7. The system of claim 1 further comprising:
  a video projector for projecting a visible light image of the body tissue based on the video image of the body tissue generated by the video imaging means; and
  a beam separator for receiving the diffuse infrared light from the output aperture and transmitting the diffuse infrared light toward the body tissue, for receiving the visible light image from the video projector and reflecting the visible light image toward the body tissue, and for receiving the infrared light reflected from the body tissue and reflecting the light reflected from the body tissue toward the video imaging means.

8. An illumination system for generating and emitting diffuse light, comprising:
  a light source for generating light; and
  means for diffusing the light, including:
    an elongate outer enclosure having a reflective inner surface, a first outer enclosure end, a second outer enclosure end, an input aperture disposed at the first outer enclosure end for receiving the light from the light source, and an output aperture disposed at the second outer enclosure end for emitting the diffuse light; and
    an elongate inner reflector disposed within the outer enclosure and between the first and second outer enclosure ends, the inner reflector having a reflective outer surface which tapers from a large end to an apex, and which reflective outer surface faces the reflective inner surface of the outer enclosure,
  the light source disposed in the input aperture of the outer enclosure for illuminating the reflective inner surface of the outer enclosure and the reflective outer surface of the inner reflector,
  the inner surface of the outer enclosure and the outer surface of the inner reflector positioned to reflect the light from the light source multiple times and in multiple directions, thereby producing diffuse light and emitting the diffuse light from the output aperture of the outer enclosure.

9. The illumination system of claim 8 wherein the elongate outer enclosure further comprises:
  a first pyramidal section having a small first pyramidal section end and a large first pyramidal section end, the first outer enclosure end incorporating the small first pyramidal section end; and
  a second pyramidal section having a large second pyramidal section end and a small second pyramidal section end, the large second pyramidal section end adjoined to the large first pyramidal section end, and the second outer enclosure end incorporating the small second pyramidal section end.

10. The illumination system of claim 9 wherein the elongate inner reflector further comprises:
  a third pyramidal section having a small third pyramidal section end and a large third pyramidal section end; and
  a tubular section having a first tubular section end and a second tubular section end, the first tubular section end adjoined to the large third pyramidal section end.

11. The illumination system of claim 8 further comprising filter means for receiving light from the light source, for transmitting infrared light having wavelengths longer than approximately 700 nanometers, and for substantially excluding light having wavelengths shorter than approximately 700 nanometers from passing into the outer enclosure.

12. An illumination system for enhancing visual contrast between bright and dark areas of an object as sensed by a direct observer of the object, the system comprising:
  an infrared light source for generating infrared light;
  means for diffusing the infrared light having a plurality of reflecting surfaces for reflecting the infrared light multiple times and in multiple directions, thereby producing diffuse infrared light, the means for diffusing the infrared light comprising:
    an elongate outer enclosure having reflective inner surfaces, and having a first outer enclosure end and a second outer enclosure end;
    an input aperture disposed at the first outer enclosure end for receiving the infrared light from the infrared light source;
    an output aperture disposed at the second outer enclosure end for receiving the diffuse infrared light reflected from the plurality of reflecting surfaces and for emitting the diffuse infrared light toward the object; and an elongate inner enclosure disposed within the outer enclosure and between the first and second outer enclosure ends, the inner enclosure having reflective outer surfaces facing the inner surfaces of the outer enclosure;

video imaging means for measuring diffuse infrared light reflected from the object in the form of an image, and for creating a video output signal representative of the image;

a video projector for receiving the video output signal from the video imaging means and for projecting visible video projector light onto the object, thereby forming a visual image which is representative of the visual image received by the video imaging means, such that the visual image projected by the video projector illuminates the object from a perspective that is the substantially the same as a perspective from which the video imaging means views the object, whereby features of the projected visual image overlay corresponding features of the object; and filter means for distinguishing between the diffuses infrared light and the visible video projector light, and for preventing the visible video projector light from reaching the video imaging means while allowing the diffuse infrared light reflected from the object to reach the video imaging means, thus eliminating positive feedback which would degrade the desired visual effect.

13. The system of claim 12 further comprising:

the elongate inner enclosure having:
   a first inner enclosure end disposed proximate the first outer enclosure end;
   a second inner enclosure end disposed proximate the second outer enclosure end; and
   an inner enclosure aperture disposed at the second inner enclosure end; and the video imaging means disposed within the inner enclosure for receiving the diffuse infrared light reflected from the object through the inner enclosure aperture.

14. The system of claim 13 further comprising the filter means disposed at the inner enclosure aperture.

15. The system of claim 12 wherein the elongate outer enclosure further comprises:
   a first pyramidal section having a small first pyramidal section end and a large first pyramidal section end, the first outer enclosure end incorporating the small first pyramidal section end;
   a second pyramidal section having a large second pyramidal section end and a small second pyramidal section end, the large second pyramidal section end adjoined to the large first pyramidal section end; and
   an outer tubular section having a first outer tubular section end and a second outer tubular section end, the first outer tubular section end adjoined to the large second pyramidal section end, the second outer enclosure end incorporating the second outer tubular end.

16. The system of claim 15 wherein the elongate inner enclosure further comprises:
   a third pyramidal section having a small third pyramidal section end and a large third pyramidal section end, the first inner enclosure end incorporating the small third pyramidal section end; and
   an inner tubular section having a first inner tubular section end and a second inner tubular section end, the first inner tubular section end adjoined to the large third pyramidal section end, and the second inner enclosure end incorporating the second inner tubular section end.

* * * * *